US010912903B2

(12) United States Patent
Fried et al.

(10) Patent No.: US 10,912,903 B2
(45) Date of Patent: Feb. 9, 2021

(54) PORTABLE DEVICE FOR AUTOMATED VENTILATION

(71) Applicant: LIFECAN MEDICAL LTD., Nazareth (IL)

(72) Inventors: Elchanan Fried, Jerusalem (IL); Moni Solomonov, New York, NY (US); Ariel Shrem, Petach Tikva (IL); Shany Rimon, Arsuf Kedem (IL); Tom Weiss-Sadan, Jerusalem (IL)

(73) Assignee: LIFECAN MEDICAL LTD., Nazareth (IL)

( * ) Notice: Subject to any disclaimer, the term of this patent is extended or adjusted under 35 U.S.C. 154(b) by 0 days.

(21) Appl. No.: 15/930,913

(22) Filed: May 13, 2020

(65) Prior Publication Data
US 2020/0353192 A1 Nov. 12, 2020

Related U.S. Application Data

(63) Continuation of application No. PCT/IL2019/050563, filed on May 19, 2019.

(60) Provisional application No. 62/674,620, filed on May 22, 2018.

(51) Int. Cl.
*A61M 16/00* (2006.01)

(52) U.S. Cl.
CPC ...... *A61M 16/0084* (2014.02); *A61M 16/024* (2017.08); *A61M 2205/3344* (2013.01); *A61M 2205/50* (2013.01); *A61M 2205/581* (2013.01); *A61M 2205/583* (2013.01); *A61M 2205/8206* (2013.01); *A61M 2230/43* (2013.01)

(58) Field of Classification Search
CPC ............ A61M 16/0084; A61M 16/024; A61M 16/0057; A61M 16/0078–0084; A61M 2205/3344; A61M 2205/50; A61M 2205/581; A61M 2205/583; A61M 2205/8206; A61M 2205/103; A61M 2205/106; A61M 2230/43; A61H 31/006
USPC .................................................. 128/204.23
See application file for complete search history.

(56) References Cited

U.S. PATENT DOCUMENTS

| 3,757,776 A | 9/1973 | Bauman |
| 3,818,806 A | 6/1974 | Fumagalli |
| 4,898,166 A | 2/1990 | Rose et al. |
| 5,222,491 A * | 6/1993 | Thomas ............ A61M 16/0084 128/205.13 |
| 5,711,295 A | 1/1998 | Harris, II |
| 6,155,257 A | 12/2000 | Lurie et al. |

(Continued)

FOREIGN PATENT DOCUMENTS

WO 2017118962 A1 7/2017

OTHER PUBLICATIONS

Al Husseini, et al., "Design and Prototyping of a Low-cost Portable Mechanical Ventilator", Proceedings of the 2010 Design of Medical Devices Conference, Apr. 13-15, 2010, Minneapolis, MN, USA; 9 pages (2010).

(Continued)

*Primary Examiner* — Valerie L Woodward
*Assistant Examiner* — Paige Kathleen Bugg
(74) *Attorney, Agent, or Firm* — The Roy Gross Law Firm, LLC; Roy Gross

(57) ABSTRACT

The present invention relates to the field of devices accommodating bag ventilators applied in medical settings, and, more particularly to devices for automation of the use of bag ventilators.

18 Claims, 11 Drawing Sheets

(56) References Cited

U.S. PATENT DOCUMENTS

| | | | |
|---|---|---|---|
| 8,534,282 B2 | 9/2013 | Bergman | |
| 2005/0284472 A1* | 12/2005 | Lin | A61M 16/0057 |
| | | | 128/202.29 |
| 2011/0041852 A1* | 2/2011 | Bergman | A61M 16/0084 |
| | | | 128/205.13 |
| 2014/0000613 A1* | 1/2014 | Hines | A61M 16/0081 |
| | | | 128/205.16 |
| 2019/0232016 A1* | 8/2019 | Sayani | A61M 16/107 |
| 2019/0336713 A1* | 11/2019 | Piracha | A61M 16/1005 |
| 2020/0086075 A1* | 3/2020 | Mujeeb-U-Rahaman | A61M 16/125 |
| 2020/0261672 A1* | 8/2020 | Pasupuleti | A61M 16/0081 |

OTHER PUBLICATIONS

Vicente, et al., "Portable automated bag-valve mask with android technology", International Journal of Advanced Technology and Engineering Exploration vol. 3(16): 28-35 (2016).

International Search Report of PCT/IL2019/050563 Completed Sep. 18, 2019; dated Sep. 19, 2019 2 pages.

Written Opinion of PCT/IL2019/050563 Completed Sep. 18, 2019; dated Sep. 19, 2019 2 pages.

* cited by examiner

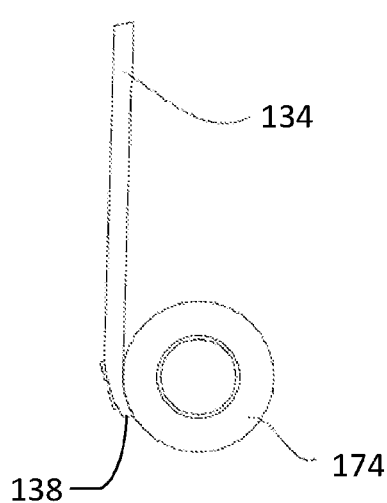
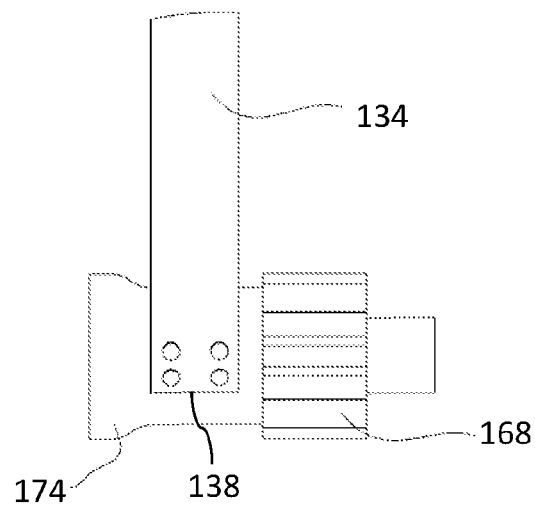
Figure 7B          Figure 7A
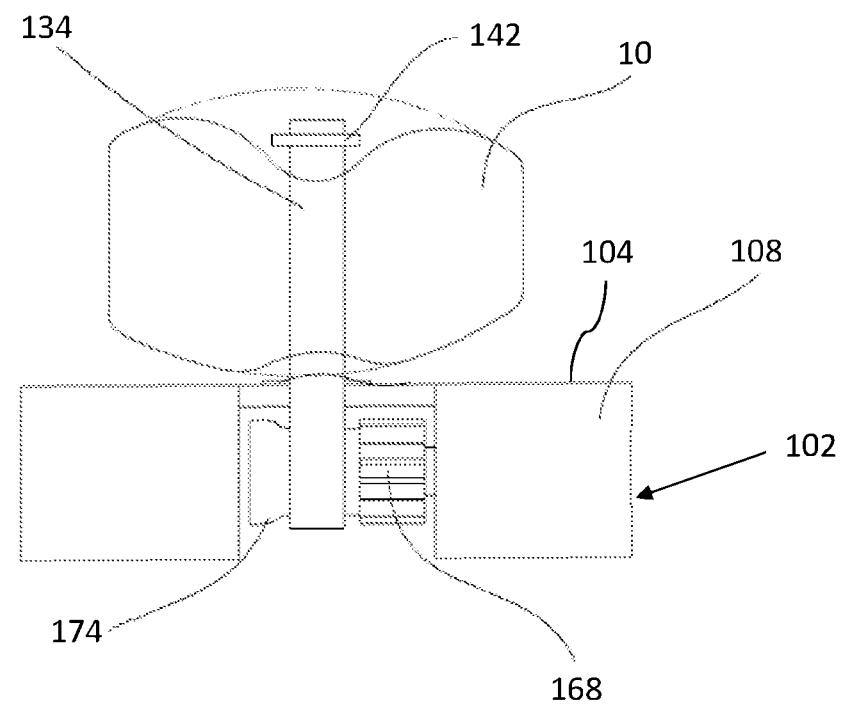
Figure 8

PORTABLE DEVICE FOR AUTOMATED VENTILATION

CROSS REFERENCE TO RELATED APPLICATIONS

This application is a Track One Continuation under the COVID19 Prioritized Pilot Program claiming priority to PCT Patent Application No. PCT/IL2019/050563 having International filing date of May 19, 2019 which claims the benefit of priority of U.S. Provisional Application No. 62/674,620 filed on May 22, 2018 entitled A PORTABLE DEVICE FOR AUTOMATED VENTILATION. The contents of the above applications are all incorporated by reference as if fully set forth herein in their entirety.

FIELD OF THE INVENTION

The present invention relates to the field of devices accommodating bag ventilators applied in medical settings, and, more particularly to devices for automation of the use of bag ventilators.

BACKGROUND OF THE INVENTION

Bag ventilators, also known as Bag Valve Masks (BVM) such as Ambu™-bags, are widely used to provide air to patients with little to no breathing efforts. Manual patient ventilation procedure usually requires at least two personnel, each using both hands: one positioned at the crown of the patient's head, maintaining airway position and mask seal with two hands, and the other encircles the bag with two hands to provide steady, regular ventilations. It is desirable to provide timely ventilations at constant time intervals. Some of the pitfalls of manual ventilation include the risk of either over-ventilating or under-ventilating. Providing too much volume or ventilating at a too-rapid rate could push air into the stomach, resulting in gastric insufflation, which in turn can lead to vomiting and subsequent airway obstruction or aspiration.

Several technologies strive to overcome the potential pitfalls of manually operated ventilation bags. U.S. Pat. No. 8,534,282 and US patent publication 2011/0041852 disclose mechanical cyclical squeezing by means of a mechanical compression squeezer, contained within a housing acting against the outer surface of an Ambu™-bag that is confined either by the housing or by confining straps. US patent application 2011/0041852 discloses a mechanical compression squeezer, which includes a flexible member that pulls hoop stresses on the exterior of a squeeze bag.

U.S. Pat. No. 5,711,295 discloses a press-like mechanism comprising two mechanical hands that hold an existing Ambu™-bag, and press against each other by the manual or mechanical operation of an attached lever. US Patent applications 2005/0284472 and 2014/0000613 disclose a compression squeezer applied to one or both sides of the bag by means of piston or clamp-like mechanisms.

U.S. Pat. No. 5,222,491 further discloses a ventilating device comprising a plurality of mechanical attachments connected to a resilient airbag, which include means for collapsing the airbag. Moreover, U.S. Pat. No. 5,222,491 provides enablement of such a device, wherein the means for collapsing the airbag include one or more guy wires connected to the inside wall of the resilient airbag. U.S. Pat. No. 4,898,166 discloses means for physically restraining the volume of an airbag, thereby determining the volume of air/gas delivered.

There is need to provide precision control of the magnitude by which bag ventilators, such as Ambu™-bags, are squeezed, in order to avoid imprecision in inhalation rate and volume achieved by manual and conventional automation assisted systems. Furthermore, it is desirable to further improve portability of such a devices without the bulkiness of an external housing into which such bags might be inserted, while avoiding risk of adding fragility or complexity to the compression mechanism.

SUMMARY OF THE INVENTION

The following embodiments and aspects thereof are described and illustrated in conjunction with systems, devices and methods which are meant to be exemplary and illustrative, not limiting in scope. In various embodiments, one or more of the above-described problems have been reduced or eliminated, while other embodiments are directed to other advantages or improvements.

According to some embodiments, there is provided a portable device for automated ventilation configured to accommodate a bag ventilator, such an Ambu™-bag, between a proximal base surface of a base body and a squeezing assembly comprising a strap. The squeezing assembly is configured to move between a released state and a pulled state, driven reciprocally by a drive mechanism attached thereto. Advantageously, the disclosed portable device for performing ventilation provides precision control of the force and speed by which a bag ventilator accommodated therein is squeezed, as well as control of cycle frequency, thereby controlling the volume and pattern of air/gas supply to a subject in need thereof.

A further advantage of the portable device disclosed herein is that it is a sturdy housing-free structure, thereby providing a reliable, compact, portable and user-friendly device. Moreover, the disclosed configuration optionally enables an operator of the device to quickly and easily switch between automated and manual bag ventilation.

According to one aspect, there is provided a portable device for automated ventilation comprising a base body having a proximal base surface.

According to some embodiments, the device further comprises a drive mechanism attached to the base body, the drive mechanism comprising an actuator and a transmission system configured to be driven thereby, and the transmission system comprising a first pulley shaft and a second pulley shaft.

According to some embodiments, the device further comprises a squeezing assembly comprising a strap, the strap comprising a first strap portion having a first strap distal end, and a second strap portion having a second strap distal end.

According to some embodiments, the first strap distal end and the second strap distal end are attached to the transmission system.

According to some embodiments, the squeezing assembly is configured to be movable between a released state and a pulled state.

According to some embodiments, the proximal base surface and the squeezing assembly are configured to accommodate a bag ventilator there between.

According to some embodiments, the first pulley shaft and the second pulley shaft are configured to be rotatable in opposite directions.

According to some embodiments, the transmission system comprises a gear train, and wherein the first pulley shaft and the second pulley shaft are rotateably attached to the gear train.

According to some embodiments, the gear train comprises a first gear connected to the actuator and rotatable thereby, a second gear interconnected with the first gear, a third gear interconnected with the first gear, and a fourth gear interconnected with the third gear.

According to some embodiments, the first pulley shaft is rigidly connected to the second gear, and the second pulley shaft is connected to the fourth gear.

According to some embodiments, the first strap distal end is rigidly attached to the first pulley shaft, and the second strap distal end is rigidly attached to the second pulley shaft.

According to some embodiments, the transmission system comprises a first transmission pulley rotateably attached to the actuator and configured to be driven thereby, a second transmission pulley, a first conveyor belt and a second conveyor belt.

According to some embodiments, the second transmission pulley is rotateably connected to the first transmission pulley via the first conveyor belt.

According to some embodiments, the first pulley shaft is rigidly attached to the second transmission pulley, and is configured to rotate in the same direction therewith.

According to some embodiments, the second pulley shaft is rotateably connected to the first pulley shaft via the second conveyor belt.

According to some embodiments, the first strap distal end is rigidly attached to a distal surface of the second conveyor belt.

According to some embodiments, the second strap distal end is rigidly attached to a proximal surface of the second conveyor belt.

According to some embodiments, the squeezing assembly is configured to reciprocate between the released state and the pulled state for a plurality of cycles.

According to some embodiments, the proximal base surface comprises a base protrusion.

According to some embodiments, the squeezing assembly further comprises a rigid member connected to the strap.

According to some embodiments, the first strap portion and the second strap portion are two distinct separate straps, and wherein the rigid member is connected to the first strap portion and the second strap portion.

According to some embodiments, the rigid member comprises a first rigid member portion and a second rigid member portion detachably attached to each other, wherein the first strap portion is rigidly connected the first rigid member portion, and wherein the second strap portion is rigidly connected the second rigid member portion.

According to some embodiments, the rigid member comprises a rigid member protrusion.

According to some embodiments, the base body further comprises a power source compartment, configured to house at least one power source.

According to some embodiments, the base body further comprises a power supply socket.

According to some embodiments, the base body further comprises a data port.

According to some embodiments, the base body further comprises a control circuitry for controlling the drive mechanism.

According to some embodiments, the base body further comprises at least one controller, configured for controlling functionality of the portable device for automated ventilation.

According to some embodiments, the base body further comprises an indication zone, configured to provide at least one visual or auditory indicator, corresponding to at least one functionality of the portable device for automated ventilation.

According to some embodiments, the base body further comprises an indication zone, configured to provide at least one visual or auditory indicator corresponding to a state of at least one characteristic of the portable device for automated ventilation.

According to some embodiments, the device further comprises at least one physiological sensing mechanism configured to measure signals related to at least one physiological characteristic of a patient.

According to some embodiments, the at least one physiological sensing mechanism comprises at least one pressure sensor.

According to some embodiments, the at least one physiological sensing mechanism comprises at least one $CO_2$ level sensor.

According to some embodiments, the device further comprises at least one operational sensing mechanism configured to measure signals related to at least one operational characteristic of portable device for automated ventilation.

According to some embodiments, the least one operational sensing mechanism comprises at least one power-level sensor.

According to some embodiments, the base body further comprises a distal base surface, the distal base surface comprising an attachment strap.

According to another aspect, there is provided a method of switching between automatic and manual bag ventilation, comprising the steps of providing the portable device for automated ventilation disclosed herein; accommodating the bag ventilator between the proximal base surface and the squeezing assembly; and initiating automatic operation of the portable device for automated ventilation, so as to reciprocally squeeze and release the bag ventilator by the drive mechanism via the squeezing assembly.

According to some embodiments, the method further comprises the step of; interrupting the automatic operation of the portable device for automated ventilation, and manually squeezing and releasing the bag ventilator by an operator's hands.

According to some embodiments, the method further comprises, manually squeezing and releasing the bag ventilator by an operator's hands prior to said initiating.

Certain embodiments of the present invention may include some, all, or none of the above advantages. Further advantages may be readily apparent to those skilled in the art from the figures, descriptions, and claims included herein. Aspects and embodiments of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The following embodiments and aspects thereof are described and illustrated in conjunction with systems, tools and methods which are meant to be exemplary and illustrative, but not limiting in scope. In various embodiments, one or more of the above-described problems have been reduced or eliminated, while other embodiments are directed to other advantages or improvements.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures:

FIG. 7A constitutes a side view of a strap portion attached to a pulley shaft, according to some embodiments.

FIG. 7B constitutes a front view of a strap portion attached to a pulley shaft, according to some embodiments.

FIG. 8 constitutes a side view of a portable device for automated ventilation with a bag ventilator in a squeezed state, according to some embodiments.

DETAILED DESCRIPTION OF SOME EMBODIMENTS

Figure 1:
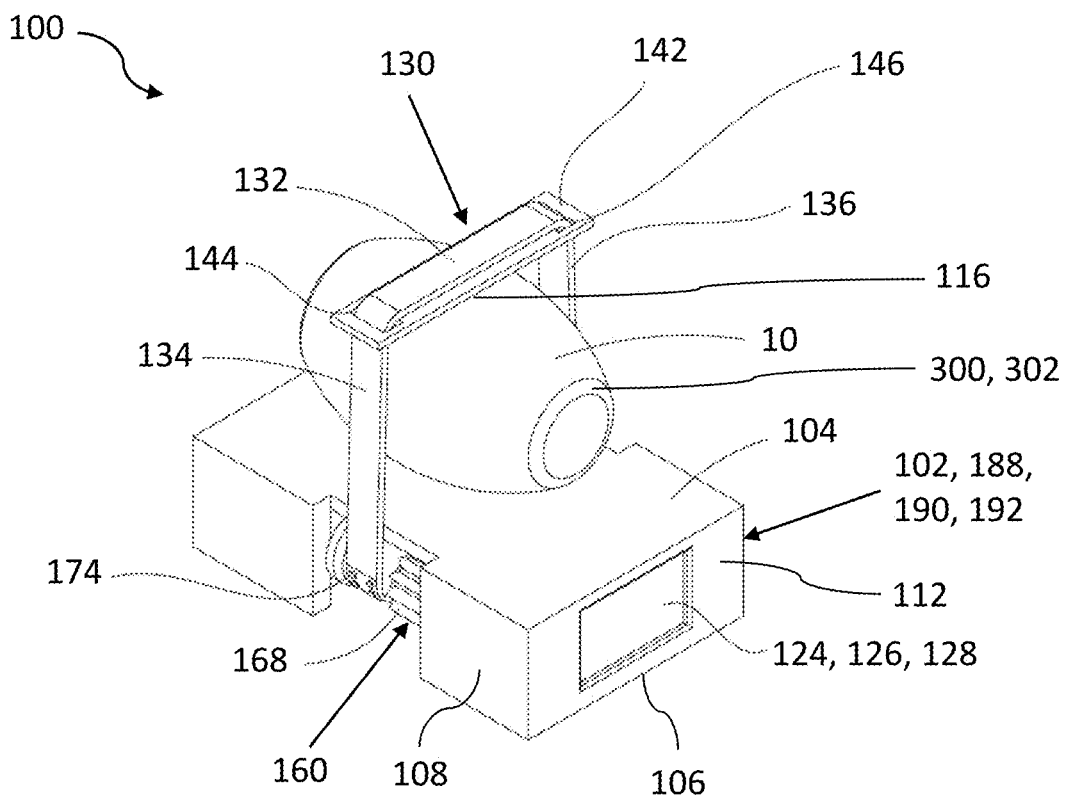
FIG. 1 constitutes a view in perspective of a portable device for automated ventilation, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. In the figures, like reference numerals refer to like parts throughout.

Figure 2:
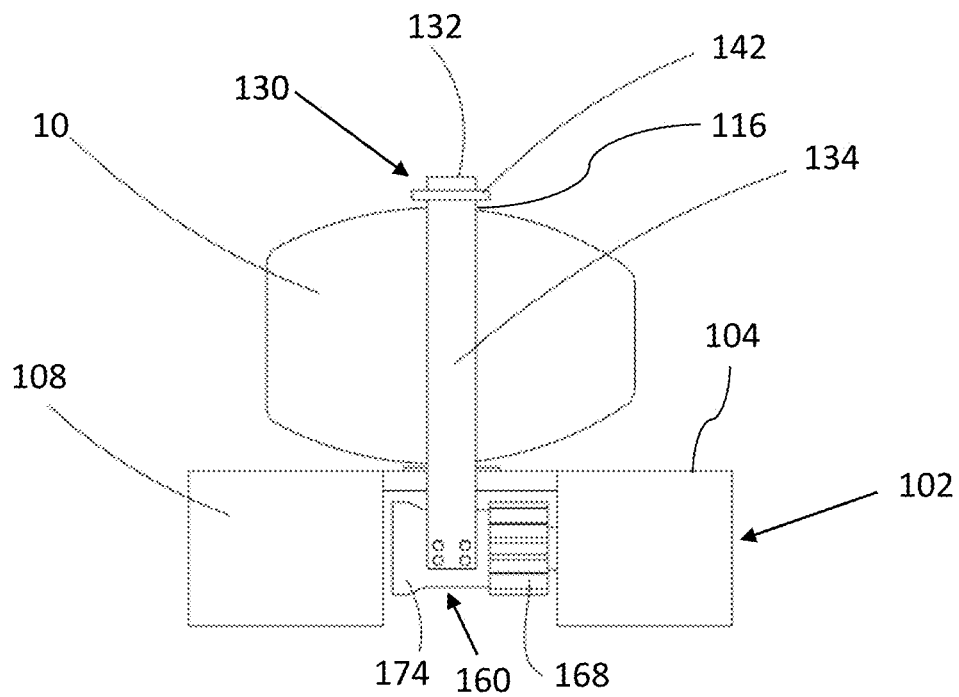
FIG. 2 constitutes a side view of a portable device for automated ventilation, according to some embodiments.
Figure 3:
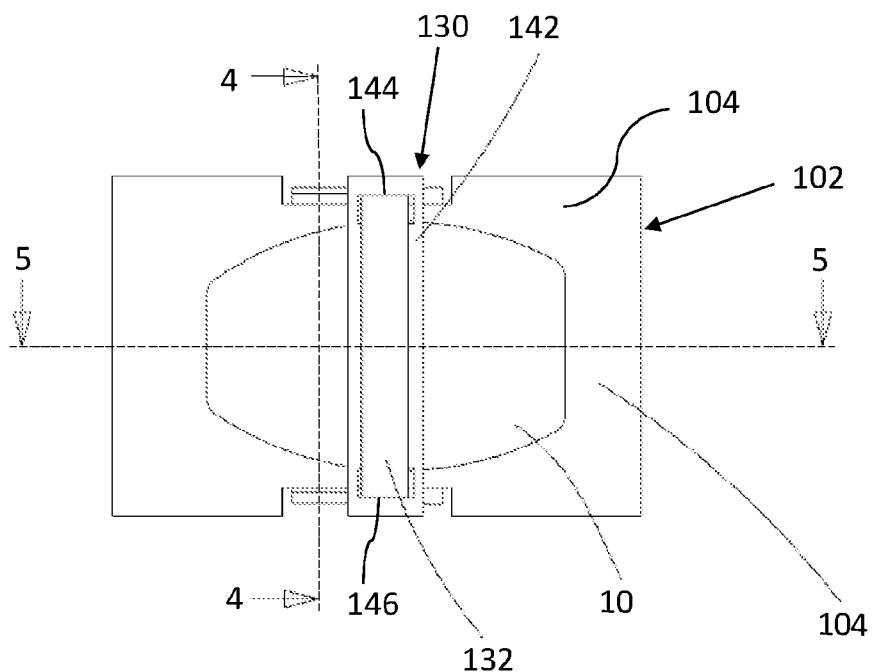
FIG. 3 constitutes a top view of a portable device for automated ventilation, according to some embodiments.
Figure 4:
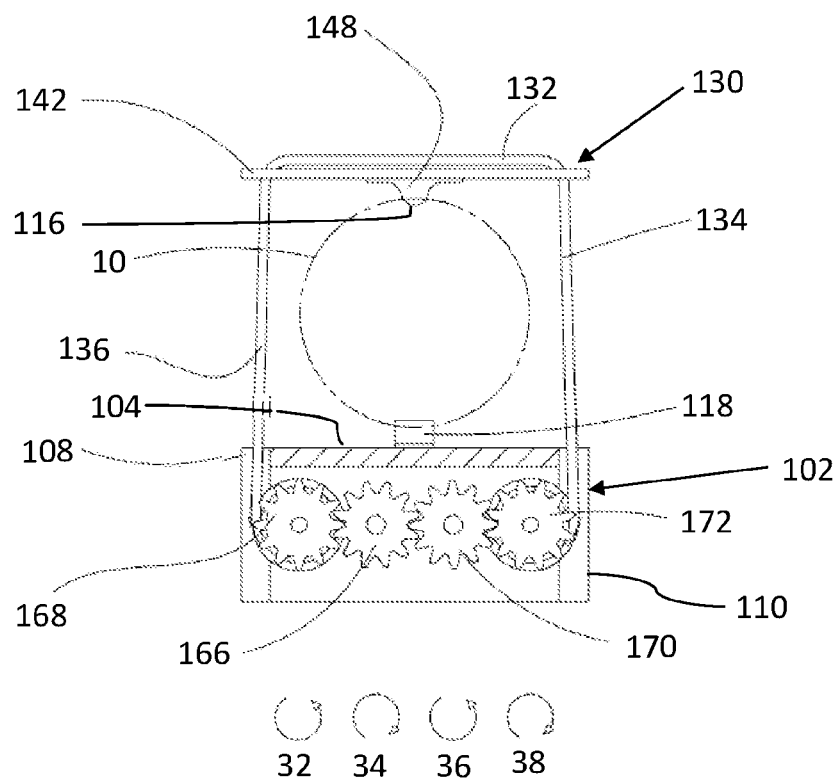
FIG. 4 constitutes a cross-sectional view of the portable device for automated ventilation of FIG. 3 along line 4-4.
Figure 5:
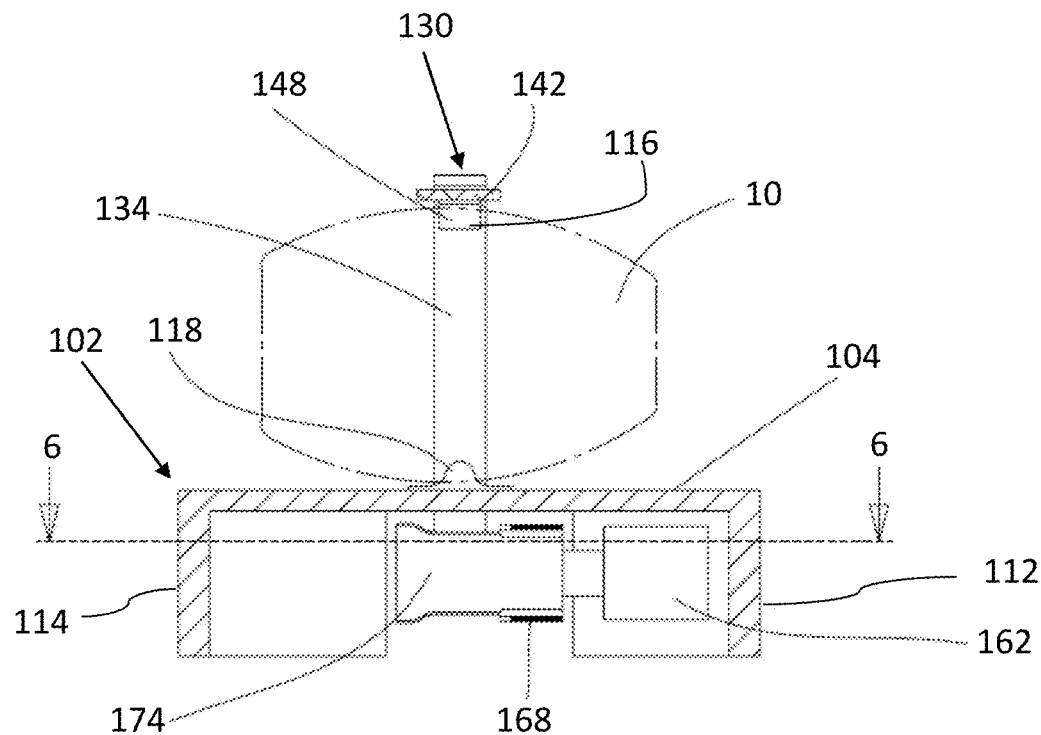
FIG. 5 constitutes a cross-sectional view of the portable device for automated ventilation of FIG. 3 along line 5-5.
Figure 6:
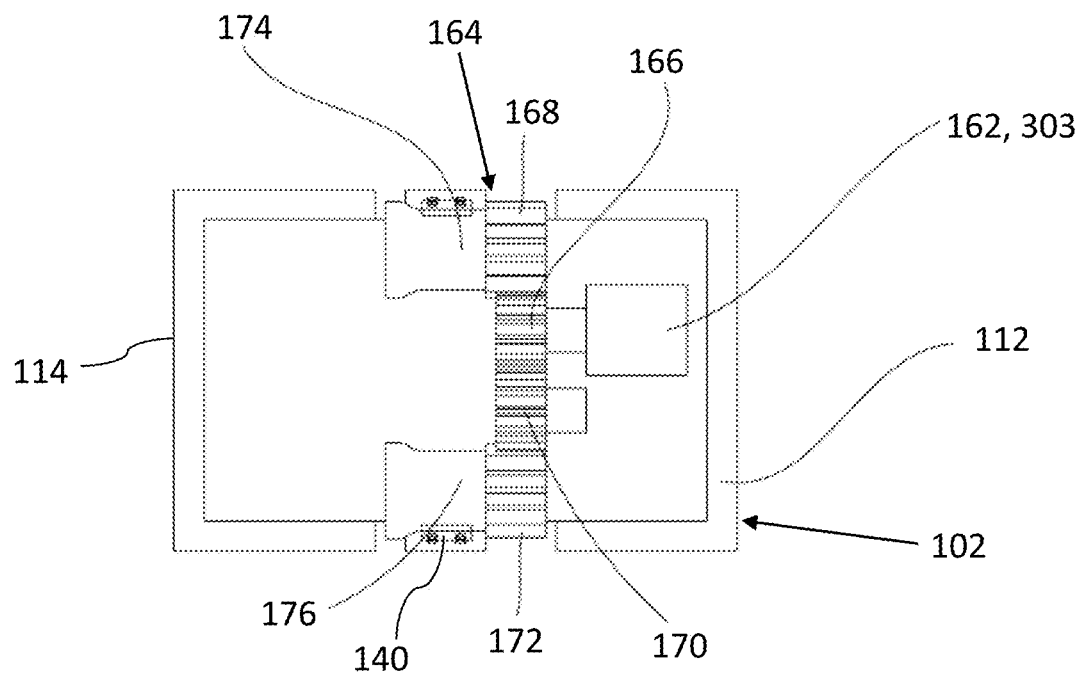
FIG. 6 constitutes a cross-sectional view of the portable device for automated ventilation of FIG. 5 along line 6-6.

Reference is now made to FIGS. 1-8. FIGS. 1, 2, and 3 constitute a view in perspective, a side view and a top view, respectively, of a portable device for automated ventilation 100, according to some embodiments. FIGS. 4 and 5 constitute cross-sectional views of portable device for automated ventilation 100 along lines 4-4 and 5-5, respectively, of FIG. 3. FIG. 6 constitutes a cross-sectional view of portable device for automated ventilation 100 along line 6-6 of FIG. 5. Portable device for automated ventilation 100 comprises a base body 102 having a proximal base surface 104, a drive mechanism 160 attached to base body 102, and a squeezing assembly 130. Squeezing assembly 130 comprises a strap 132 having a first strap portion 134 (see FIGS. 7A-B) and a second strap portion 136. First strap portion 134 comprises a first strap distal end 138, and second strap portion 136 comprises a second strap distal end 140. Drive mechanism 160 comprises an actuator 162 and a transmission system 164. First strap distal end 138 and second strap distal end 140 are attached to transmission system 164.

The term "strap", as used herein, refers to any elongated flexible structure known in the art, capable of being wrapped and unwrapped around rods or pulleys, such as a strap, a cord, a cable, a chain and the like.

The term "portable", as used herein in relation to device 100, refers to a device 100 being sufficiently light and small that it can be carried by a single adult.

The terms "portable device for automated emergency ventilation", portable device for automated ventilation" and "device", as used herein, are interchangeable.

The term "bag ventilator", as used herein, also known as Bag Valve Mask (BVM), manual resuscitator of self-inflating bag, refers to ambulatory or movable bags which are manually squeezable to provide or assist in respiration of a patient, such as, but not limited to, Ambu™-bags.

According to some embodiments, portable device for automated ventilation 100 is configured to operate as a portable device for automated ventilation 100, during emergency situations.

Proximal base surface 104 and squeezing assembly 130 are configured to accommodate a bag ventilator 10 when placed there between. Bag ventilator 10 is termed to be "accommodated" within device 100, between proximal base surface 104 and squeezing assembly 130, when at least a portion of bag ventilator 10 rests upon and is in contact with proximal base surface 104, and when at least a portion of squeezing assembly 130 is pressed against bag ventilator 10 at squeezing assembly contact region 116, opposite thereto.

Portable device for automated ventilation 100, as disclosed in any of the embodiments throughout the current disclosure, does not include bag ventilator 10, but is configured to accommodate bag ventilator 10 therein.

Advantageously, portable device for automated ventilation 100, as disclosed in any of the embodiments throughout the current disclosure, is devoid of any housing surrounding bag ventilator 10. Thus, device 100 which is not configured to house bag ventilator 10 between at least three rigid sidewalls, but rather accommodate it between one base surface and a squeezing assembly, provides a compact, portable and user-friendly structure. Moreover, the disclosed configuration enables an operator of the device to quickly and easily switch between automated and manual bag ventilation.

Within the context of this application, the term "proximal" generally refers to the side or end of any device or a component of a device, which is closer to the contact region of squeezing assembly contact region 116.

Within the context of this application, the term "distal" generally refers to the side or end of any device or a component of a device, which is opposite the "proximal" side, and is farther from squeezing assembly contact region 116.

Within the context of this application, the term "proximal direction" refers to a direction pointing towards squeezing assembly contact region 116, and the term "distal direction" refers to an opposite direction pointing away from squeezing assembly contact region 116. For example, arrows 22 and 24 in FIG. 11 correspond to a distal direction.

Within the context of this application, the term "lateral plane" generally refers to any plane perpendicular to the proximal direction or the distal direction.

Within the context of this application, the term "lateral direction" refers to any possible direction along a lateral plane.

According to some embodiments, base body 102 further comprises a distal base surface 106, and at least two sidewalls and two panels connecting proximal base surface 104 with distal base surface 106, such as first base sidewall 108, second base sidewall 110, first base panel 112 and second base panel 114.

According to some embodiments, proximal base surface 104 is formed as a flat surface (see FIG. 1). According to some embodiments, proximal base surface 104 is curved (embodiment not shown in FIGS. 1-8). According to some embodiments, proximal base surface 104 is dimensioned and shaped so as to accommodate the shape of bag ventilator 10. According to some embodiments, proximal base surface 104 is dimensioned and shaped so as to accommodate the shape of bag ventilator 10, such that when bag ventilator 10 is placed upon proximal base surface 104, its movement in any lateral direction is constricted (one such example presented in FIGS. 9A-D).

According to some embodiments, proximal base surface 104 is lined with friction increasing material, such as, but not limited to, rubber.

According to some embodiments, base body 102 is shaped as a rectangular compartment (embodiment not shown). According to some embodiments, at least one of first base sidewall 108 or second base sidewall 110 is formed with at least one discontinuity (see FIGS. 1-3, discontinuity not numbered). According to some embodiments, at least one of first base panel 112 or second base panel 114 is formed with at least one discontinuity. According to some embodiments, at least one of first base sidewall 108, second base sidewall 110, first base panel 112, second base panel 114, proximal base surface 104 and distal base surface 106, is formed with a combination of straight or curved surfaces (see FIGS. 9A-9D). According to some embodiments, base body 102 is comprises at least one internal hollow compartment, configured to accommodate driving mechanism 160 therein.

Drive mechanism 160 comprises an actuator 162 and a transmission system 164, configured to be driven thereby. Transmission system 164 comprises a first pulley shaft 174 and a second pulley shaft 176. According to some embodiments, transmission system further comprises a gear train, wherein first pulley shaft 174 and second pulley shaft 176 are rotateably attached to the gear train.

According to some embodiments, first pulley shaft 174 and second pulley shaft 176 are configured to be rotatable in opposite directions.

The term "actuator", as used herein, refers to any powered actuator known in the art for providing rotational motion, such as an electric motor, a solenoid, and the like.

According to some embodiments, the gear train of transmission system 164 comprises at least a first gear 166 connected to actuator 162 and rotatable thereby. According to some embodiments, the gear train of transmission system 164 comprises a plurality of gears. In the example depicted in FIGS. 4-6, the gear train of transmission system 164 comprises four gears: first gear 166, second gear 168, third gear 170 and fourth gear 172. First gear 166 is connected to actuator 162, for example via a shaft (see FIGS. 5-6, shaft not numbered). Second gear 168 and third gear 170 are interconnected with first gear 166, such that when first gear rotates in the direction of arrow 34 (see FIG. 4), Second gear 168 and third gear 170 rotate in direction 32 and 36, respectively. Fourth gear 172 is interconnected with third gear 170, such that when third gear 170 is rotated in direction 36, fourth gear rotates in direction 38.

According to some embodiments, each one of first pulley shaft 174 and second pulley shaft 176 is rigidly connected to a different gear. In the example depicted in FIGS. 4-6, first pulley shaft 174 is rigidly connected to second gear 168 and rotatable therewith in the same direction 32, and second pulley shaft 176 is rigidly connected to fourth gear 172 and rotatable therewith in the same direction 38.

First strap portion 134 and second strap portion 136 are moveable, either directly or via intermediary components, to first pulley shaft 174 and second pulley shaft 176, respectively. According to some embodiments, first strap distal end 138 is rigidly attached to first pulley shaft 174 (see FIGS. 7A-7B), and second strap distal end 140 is rigidly attached to second pulley shaft 176.

Squeezing assembly 130 is configured to be movable between a released state and a pulled state. In a released state, squeezing assembly contact region 116 is distanced from proximal base surface 104 such that bag ventilator 10, when accommodated there between, is normally expanded. In a pulled state, the distance between squeezing assembly contact region 116 and proximal base surface 104 is shorter than such distance in the released state, such that bag ventilator 10, when accommodated there between, is squeezed.

In use, when bag ventilator 10 is accommodated within device 100 and squeezing assembly 130 is in a released state, actuator 162 is actuated so as to drive transmission system 164. First pulley shaft 174 and second pulley shaft 176 are configured to rotate in opposite directions to one another, thereby pulling first strap portion 134 and second strap portion 136 in the distal direction, towards a pulled state of squeezing assembly 130. During transition from a released state to a pulled state, first strap portion 134 and second strap portion 136 are wrapped around first pulley shaft 174 and second pulley shaft 176, respectively. When squeezing assembly 130 is in a pulled state, actuator 162 stops driving gear train transmission system 164, such that the gears of the gear train, along with first pulley shaft 174 and second pulley shaft 176, are free to rotate in any direction. Squeezed bag ventilator 10 is self-inflating to its normally expanded form, pushing against squeezing assembly contact region 116, thereby extending first strap portion 134 and second strap portion 136 in the proximal direction, towards a released state of squeezing assembly 130, while first strap portion 134 and second strap portion 136 are unwrapped from first pulley shaft 174 and second pulley shaft 176, respectively.

The term "squeezed", as used herein in relation to bag ventilator 10, refers to a bag ventilator 10 with decreased volume. The term "normally expanded", as used herein in relation to bag ventilator 10, refers to an un-collapsed or un-squeezed state of bag ventilator 10.

The term "self-inflating", as used herein in relation to bag ventilator 10, refers to a bag ventilator 10 increasing in volume to a normally expanded state.

According to some embodiments, squeezing assembly 130 is configured to reciprocate between the released state and the pulled state for a plurality of cycles.

The term "cycle", as used herein, refers to squeezing and releasing bag ventilator 10.

The term "plurality", as used herein, refers to more than one.

According to some embodiments, squeezing assembly 130 is configured to reciprocate between the released state and the pulled state for a predetermined number of cycles. According to some embodiments, squeezing assembly 130 is configured to reciprocate between the released state and the pulled state until stopped by an operator of device 100. According to some embodiments, squeezing assembly 130 is configured to reciprocate between the released state and the pulled state until an external trigger is received, such as a physiological reading of a patient, exceeding a predetermined threshold.

In the example depicted in FIGS. 4-7B, actuator 162 rotates first gear 166 in the direction of arrow 34, which translates to a rotation of second gear 168 along with first pulley shaft 174 in direction 32, opposite to direction 34, and to a rotation of fourth gear 172 (via third gear 170) along with second pulley shaft 176 in direction 38, identical to direction 34. First strap portion 134 and second strap portion 136, rigidly attached at first strap distal end 138 to first pulley shaft 174, and at second strap distal end 140 to second pulley shaft 176, respectively, are wrapped around first pulley shaft 174 and second strap distal end 174, respectively, thereby pulling squeezing assembly contact region 116 of squeezing assembly 130 in the distal direction. Squeezing assembly 130, pressed against bag ventilator 10, squeezes bag ventilator 10 to a squeezed state thereof.

When squeezing, assembly 130 is in a pulled state, first gear 166 is no longer rotated by actuator 162, and all gears of transmission system 164 are free to rotate in any direction. As no additional force is exerted by squeezing assembly 130 on bag ventilator 10, bag ventilator 10 is free to expand, due to its nature, back to the normally expanded state thereof. During self-inflation of bag ventilator 10, squeezing assembly contact region 116 is forced to move away from proximal base surface 104, in the distal direction, while first strap portion 134 and second strap portion 136 are unwrapped from first pulley shaft 174 and second strap distal end 174, respectively.

According to some embodiments, squeezing assembly 130 comprises a single strap 132, wherein first strap portion 134 and second strap portion 136 constitute two portions of the same strap 132. According to some embodiments, strap 132 is lined with friction increasing material, such as, but not limited to, rubber.

According to some embodiments, strap 132 is configured to wrap around at least a portion of a circumference of bag ventilator 10 when accommodated within device 100 (embodiment not shown).

According to some embodiments, first strap portion 134 and second strap portion 136 form two distinct separate straps, permanently attached or detachably attached to each other, either directly or indirectly.

According to some embodiments, squeezing assembly 130 further comprises a rigid member 142 connected to strap 132 (see FIGS. 1-5). According to some embodiments, squeezing assembly 130 further comprises a rigid member 142 connected to distinct separate first strap portion 134 and second strap portion 136 (embodiment not shown in FIGS. 1-8), such that first strap portion 134 and second strap portion 136 are indirectly attached to each other via rigid member 142.

According to some embodiments, rigid member 142 comprises a first slit 144 and a second slit 146, through which strap 132 is laced. It will be clear to a skilled person in the art that any other methods known in the art for attaching either one of strap 132, first strap portion 134 or second strap portion 136, with rigid member 142, are applicable, such as gluing, riveting and the like.

Rigid member 142 is configured to press against bag ventilator 10 when accommodated within device 100, squeezing it when squeezing assembly 130 moves from a released state to a pulled state, and pushable by bag ventilator 10 when squeezing assembly 130 moves from a pulled state to a released state.

Advantageously, having rigid member 142 comprised within squeezing assembly 130 enables more homogenous force dispersing across bag ventilator 10 when squeezed, and more homogenous force dispersing acting on squeezing assembly 130 when bag ventilator 10 self-inflates, relative to a squeezing assembly 130 having a strap 132 configured to directly abut at least a portion of bag ventilator 10. Moreover, rigid member 142 is configured to apply gradual squeezing force on bag ventilator 10, since the region of direct contact between rigid member 142 and bag ventilator 10 gradually expands as bag ventilator 10 is further squeezed thereby.

According to some embodiments, rigid member 142 is lined with friction increasing material, such as, but not limited to, rubber.

According to some embodiments, proximal base surface 104 further comprises base protrusion 118 (see FIGS. 4-5), protruding in the proximal direction, configured to press against bag ventilator 10 when accommodated within device 100. According to some embodiments, rigid member 142 further comprises rigid member protrusion 148 (see FIGS. 4-5), protruding in the distal direction, configured to press against bag ventilator 10 at squeezing assembly contact region 116 when accommodated within device 100.

Advantageously, any of base protrusion 118 or rigid member protrusion 148 reduce the magnitude of force required to squeeze bag ventilator 10 when squeezing assembly 130 is in the released state. A further advantage of having rigid member 142 comprised within squeezing assembly 130, is that it provides the option to include rigid member protrusion 148 therein.

FIG. 8 depicts an exemplary portable device for automated ventilation 100 with bag ventilator 10 accommodated therein, both in a squeezed state (solid lines) and a normally expanded state (dashed lines) thereof.

While FIGS. 4-6 depict embodiments of a specific transmission system 164 implemented with a gear train having four gears, it will be understood by those skilled in the art that other transmission systems can be implemented, including any set of interworking gears, cogwheels, racks, bearings, screws, chains, shafts, pulleys and conveyor belts, configured to transform rotational motion of actuator 162 to rotational motion of first pulley shaft 174 and of second pulley shaft 176 in desired directions.

According to some embodiments, device 100 further comprises control circuitry 303 (see FIGS. 6 and 10), configured to control drive mechanism 160. According to some embodiments, base body 102 further comprises at least one interface panel 124 (see FIG. 1). According to some embodiments, the at least one interface panel 124 comprises at least one controller 126 (see FIG. 1), configured to enable an operator of device 100 to control at least one functionality thereof. It will be clear that any controller-types known in the art are applicable, such as, but not limited to: a switch, a button, a knob, a lever, a touch-interface, a proximity sensor, and an auditory controlled command receiver.

According to some embodiments, the at least one controller 126 comprises a power on/off switch. According to some embodiments, the at least one controller 126 comprises a start/stop switch. According to some embodiments, the at least one controller 126 comprises a selector between different modes of operation, controlling at least one of: squeezing force or pressure applied by squeezing assembly 130 on bag ventilator 10, squeezing speed for moving squeezing assembly 130 from a released state to a pulled state, and cycle frequency. According to some embodiments, the selector is configured to switch between predefined modes adapted for ventilating different patient-types, such as: children, small adults, and large adults (defined as adults weighing less or more than a predefined weight threshold).

According to some embodiments, at least one interface panel 124 comprises indication zone 128 (see FIG. 1), configured to provide at least one visual or auditory indicator, corresponding to at least one functionality of portable device for automated ventilation 100.

According to some embodiments, at least one interface panel 124 comprises indication zone 128 128, configured to provide at least one visual or auditory indicator, corresponding to the state of at least one characteristic of portable device for automated ventilation 100, such as power status.

While at least one interface panel 124 is depicted in FIG. 1 as being located on first base panel 112, it will be clear to a person skilled in the art that interface panel 124 can be located on any other portion of base body 102, as long as it is accessible to an operator of device 100. According to some embodiments, base body 102 comprises a plurality of interface panels 124 (embodiment not shown in FIGS. 1-8).

The term "cycle frequency", as used herein, refers to the frequency of squeezing and releasing bag ventilator 10.

According to some embodiments, base body 102 further comprises a power source compartment 188 (see FIG. 1), configured to house at least one power source (not shown). The at least one power source is configured to provide power to at least one of: actuator 162, control circuitry, and at least one interface panel 124. According to some embodiments, power source compartment 188 is configured to house at least one disposable power source, such as a battery.

According to some embodiments, power source compartment 188 is configured to house at least one rechargeable power source, such as a rechargeable battery. According to some embodiments, base body 102 further comprises a receiver unit (not shown) configured for receiving energy from an external base unit (not shown) via an inductive magnetic field, wherein the at least one rechargeable power source is capable of being inductively powered and/or charged by the receiver unit.

As used herein, the term "energy" refers to electrical energy such as electricity or power. Energy is quantified in e.g. Watt-hour, Ampere-hour, or Joule.

According to some embodiments, base body 102 further comprises a power supply socket 190 (see FIG. 1), configured to connect with a power charging or power supplying cable (not shown). The power charging or power supplying cable, when connected to power supply socket 190 and electrically connected to an external power source (not shown), is configured to either supply power to recharge at least one rechargeable power source, to supply power directly to the actuator 162, or both.

According to some embodiments, power supply socket 190 comprises a USB charging port configured for receiving a USB cable (not shown). The USB cable, when connected to the USB charging port, serves as a power charging cable in a similar manner described hereinabove.

According to some embodiments, base body 102 further comprises a data port 192 (not shown in FIGS. 1-8). According to some embodiments, data port 192 comprises a USB port configured to receive a USB device for retrieving data therefrom, writing data thereto, or both.

Figure 9A:
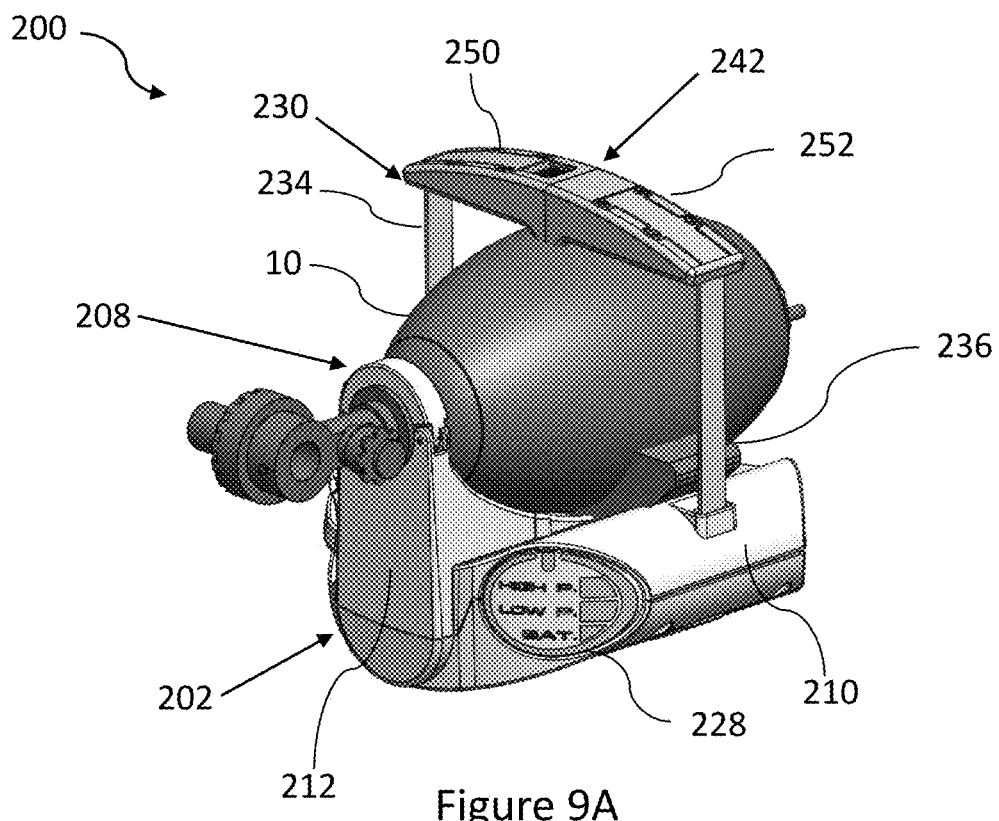
FIG. 9A constitutes a view in perspective of a portable device for automated ventilation, from a front-right angle, according to some embodiments.
Figure 9B:
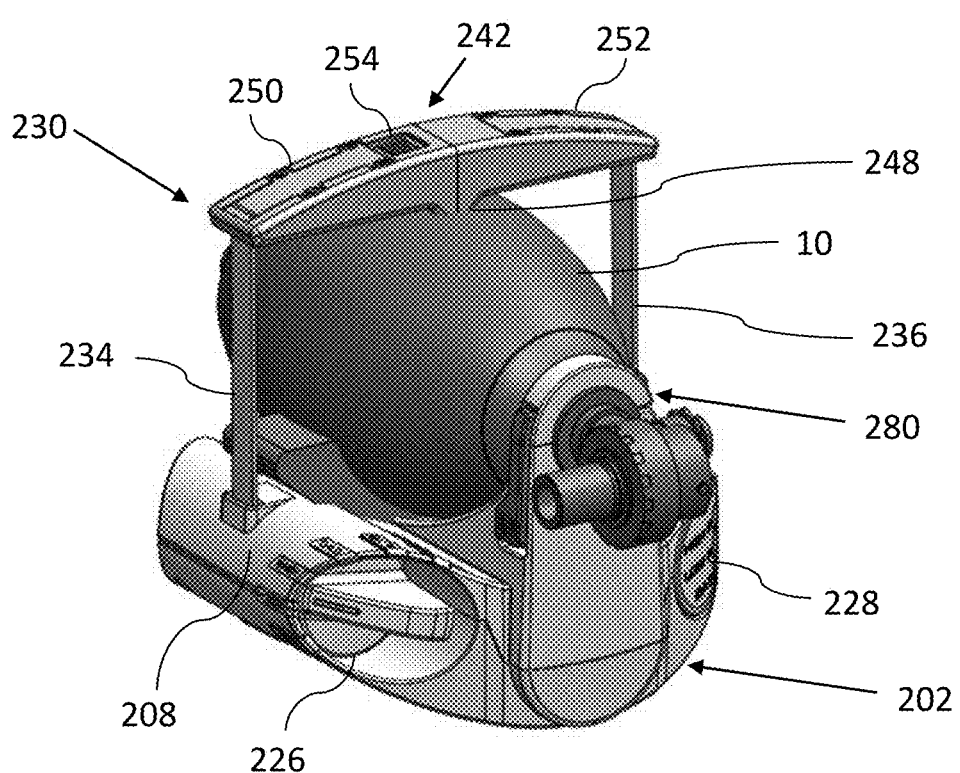
FIG. 9B constitutes a view in perspective of a portable device for automated ventilation, from a front-left angle, according to some embodiments.
Figure 9C:
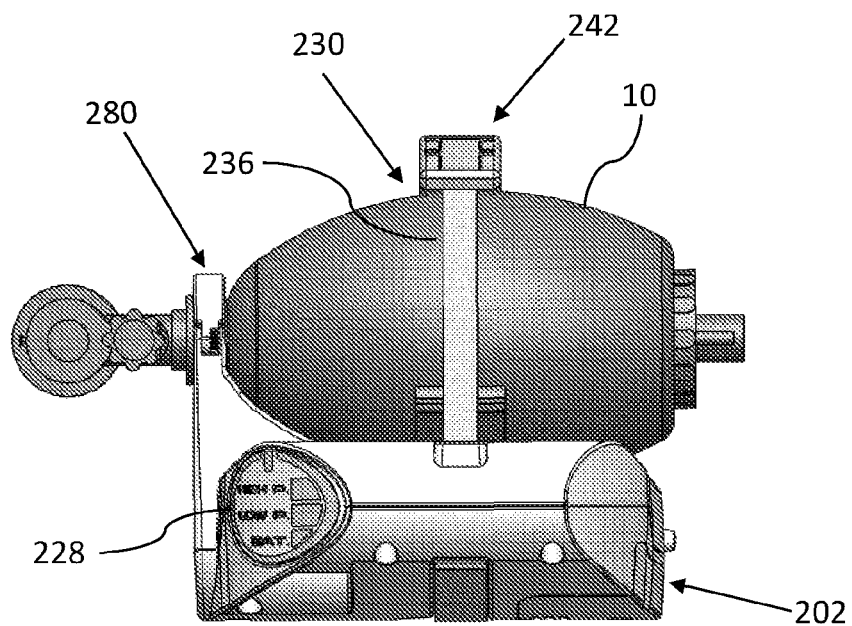
FIG. 9C constitutes a perspective side view of a portable device for automated ventilation, according to some embodiments.
Figure 9D:
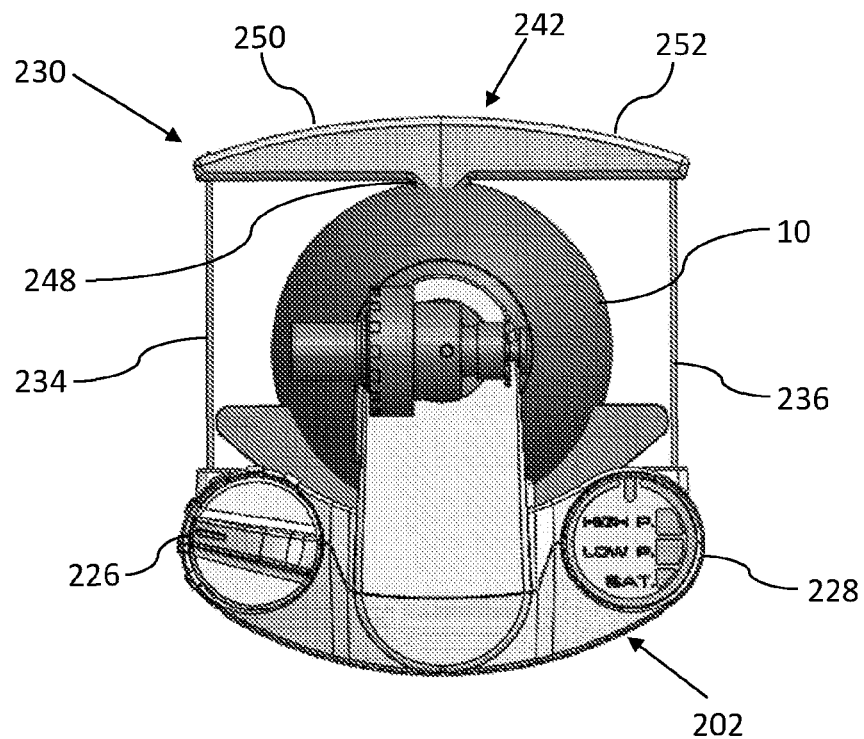
FIG. 9D constitutes a perspective front view of a portable device for automated ventilation, according to some embodiments.
Figure 10:
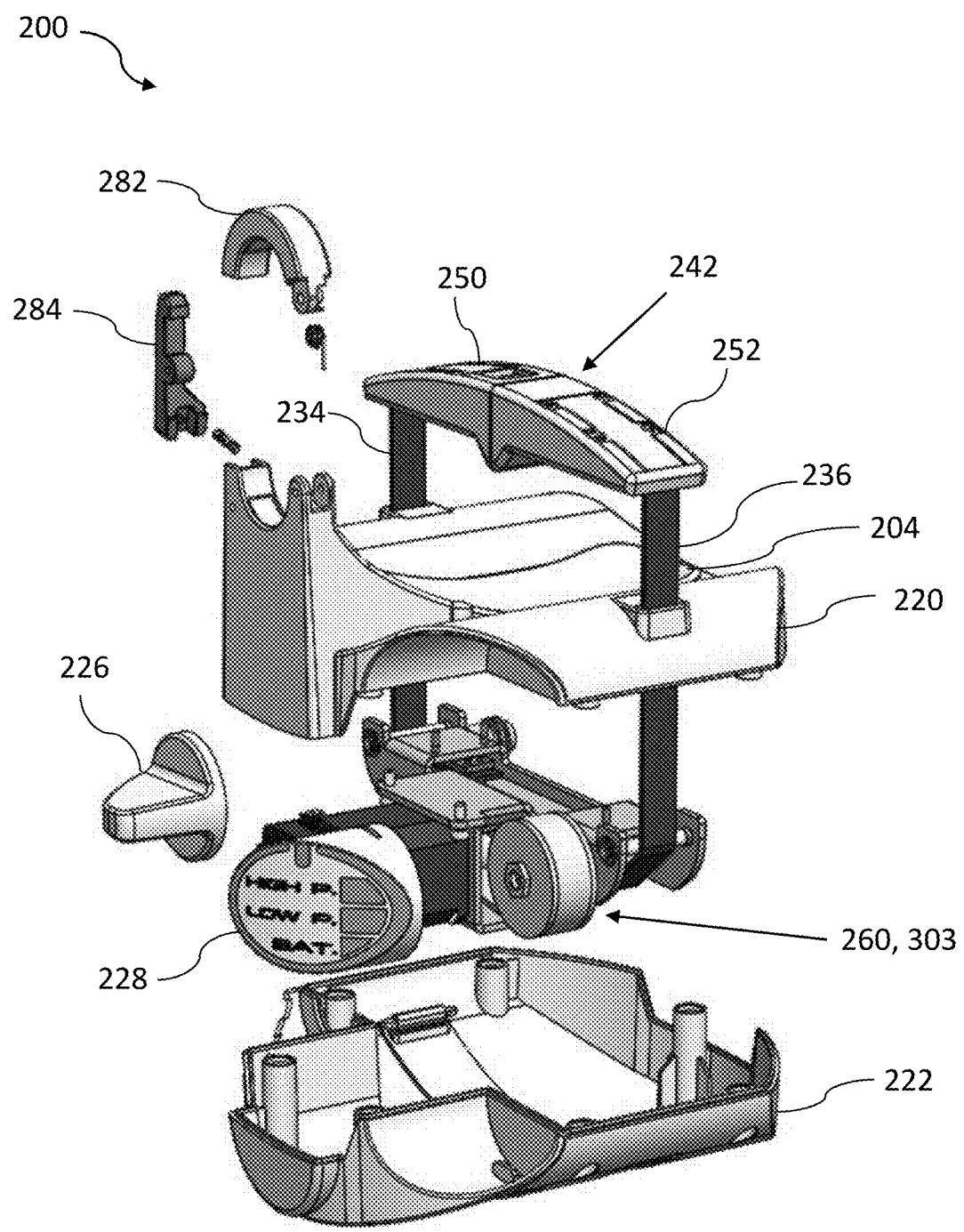
FIG. 10 constitutes an exploded view in perspective of a portable device for automated ventilation, according to some embodiments.
Figure 11:
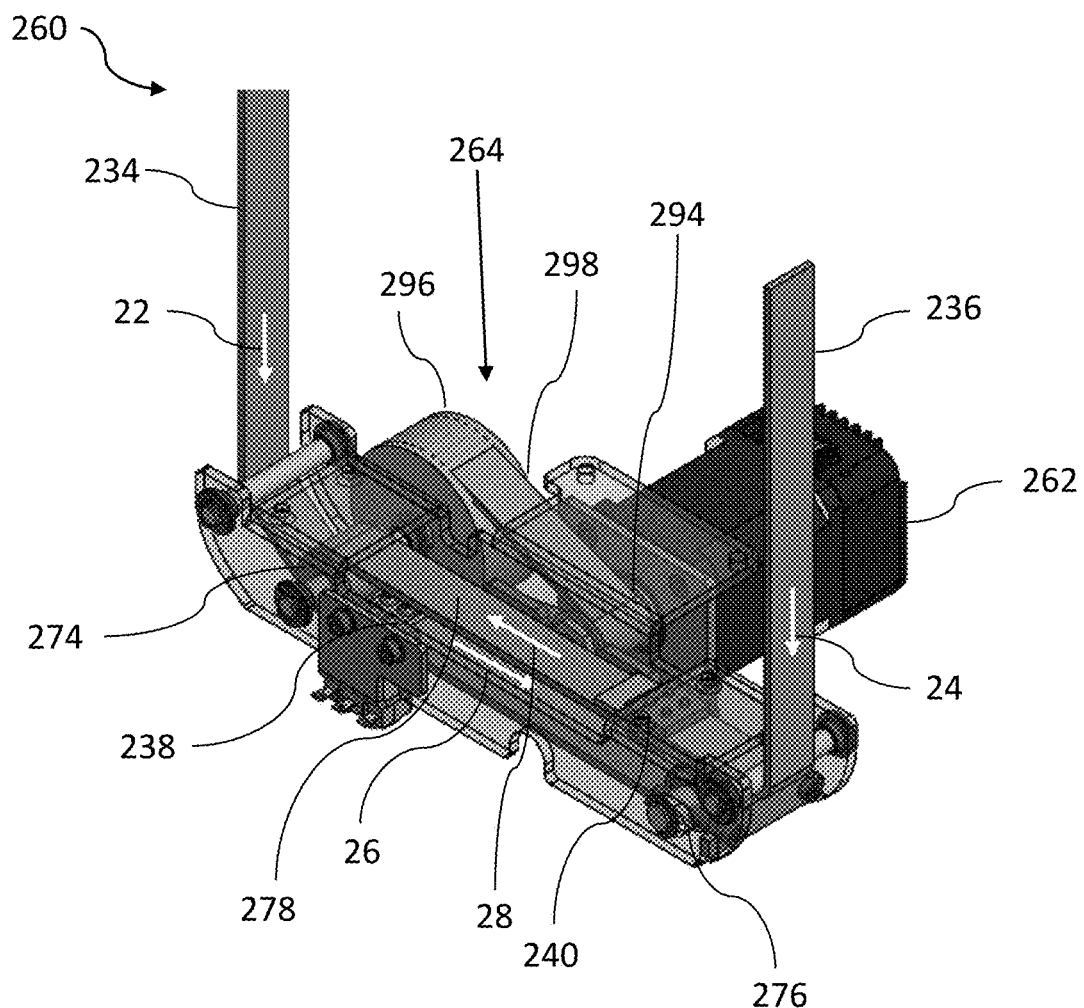
FIG. 11 constitutes a partial view in perspective of a drive mechanism of a portable device for automated ventilation, according to some embodiments.
Figure 15A:
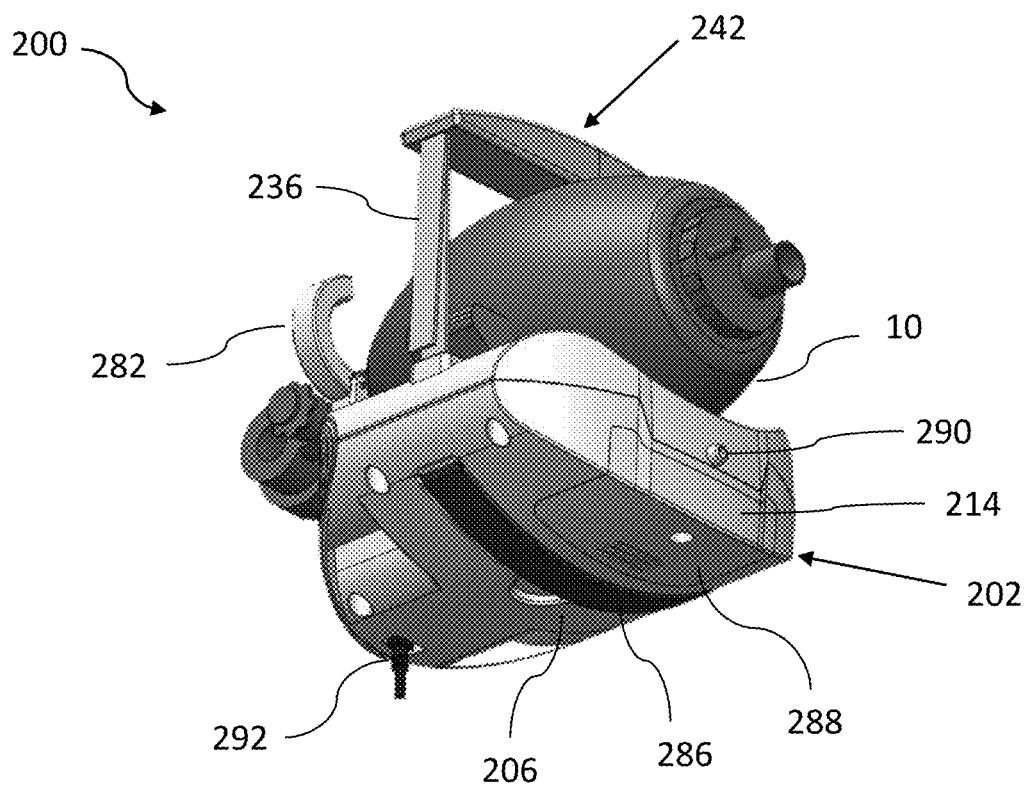
FIG. 15A constitutes a view in perspective of a portable device for automated ventilation, from a rear-bottom angle, according to some embodiments.
Figure 15B:
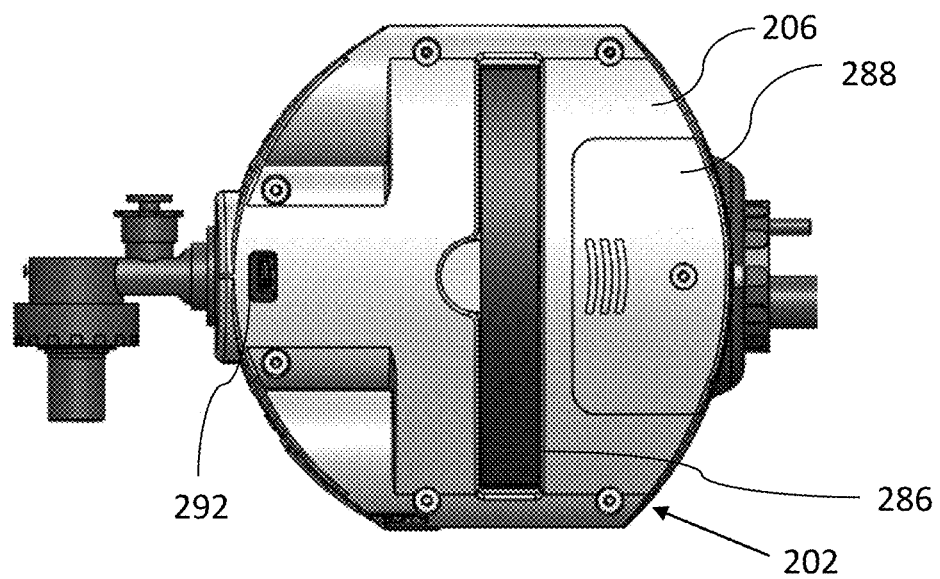
FIG. 15B constitutes a perspective bottom view of a portable device for automated ventilation, from a rear-bottom angle, according to some embodiments.

Reference is now made to FIGS. 9-15B8. FIGS. 9A, 9B, 9C, 9D and 10 constitute a view in perspective from a front-right angle, a view in perspective from a front-left angle, a perspective side view, a perspective front view and an exploded view, respectively, of portable device for automated ventilation 200, according to some embodiments. Portable device for automated ventilation 200 comprises base body 202 having proximal base surface 204, drive mechanism 260 attached to and housed within base body 202 and squeezing assembly 230. FIG. 11 constitutes a partial view in perspective of drive mechanism 260.

According to some embodiments, as depicted in FIGS. 9A-15B, base body 202 further comprises distal base surface 206, first base sidewall 208, second base sidewall 210, first base panel 212 and second base panel 214. According to some embodiments (see FIG. 10), base body 202 comprises a proximal base enclosure 220 and a distal base enclosure 222 attached to each other, thereby forming an internal hollow compartment configured to accommodate drive mechanism 260 therein.

Squeezing assembly 230 comprises first strap portion 234 having first strap distal end 238, and second strap portion 236 having second strap distal end 240, wherein first strap portion 234 and second strap portion 236 are two distinct separate straps. First strap distal end 238 and second strap distal end 240 are attached to drive mechanism 260. According to some embodiments, as depicted in FIGS. 9A-10, squeezing assembly 230 further comprises rigid member 242 which comprises a first rigid member portion 250 and a second rigid member portion 252, detachably attached to each other. First strap portion 234 is rigidly connected to first rigid member portion 250 at an end opposite to first strap distal end 238, and second strap portion 236 is rigidly connected to second rigid member portion 252 at an end opposite to second strap distal end 238.

Figure 14A:
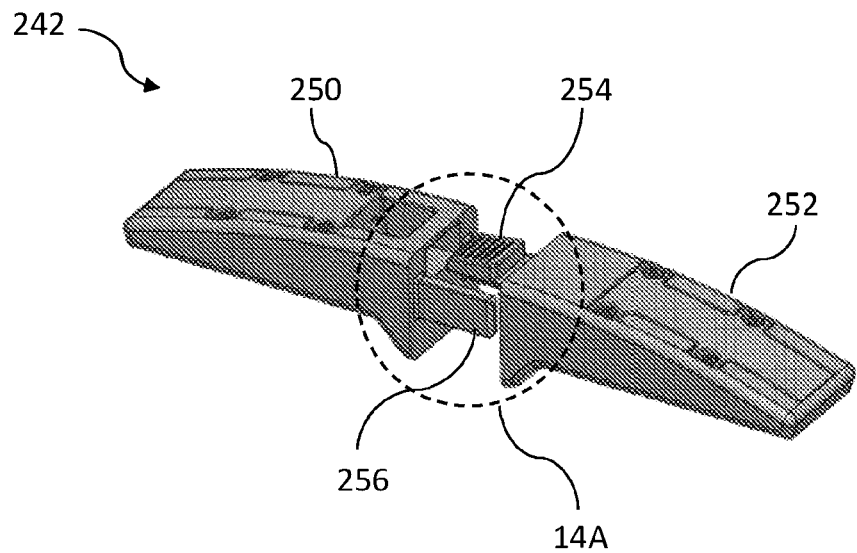
FIG. 14A constitutes a view in perspective of a rigid member having a first rigid member portion and a second rigid member portion separated from each other, according to some embodiments.
Figure 14B:
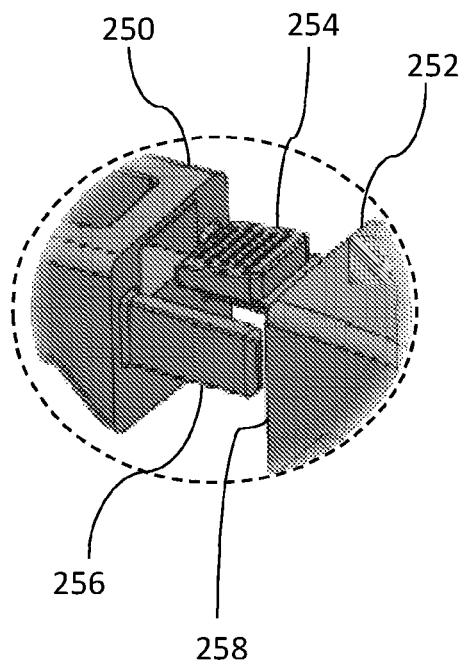
FIG. 14B constitutes a zoom-in view or region 14B marked in FIG. 14A.

FIG. 14A constitutes a view in perspective of rigid member 242 having first rigid member portion 250 and second rigid member portion 252 separated from each other. According to some embodiments, first rigid member portion 250 and second rigid member portion 252 are detachably connected to each other via an attachment mechanism. An exemplary attachment mechanism depicted in FIG. 14A and zoomed-in in FIG. 14B, is a snap-fit mechanism. In the example depicted in FIG. 14A-B, second rigid member portion 252 comprises a snap/release button 254, configured to be received within a matching receptacle (not numbered) in first rigid member portion 250. In use, first rigid member portion 250 and second rigid member portion 252 can be attached to each other by snapping snap/release button 254 into the matching receptacle, and can be detached from each other by pressing snap/release button 254 and pulling them away from one another.

In the example depicted in FIGS. 14A-B, first rigid member portion 250 further comprises at least one guiding pin 256, such as the two guiding pins 256 depicted in FIGS. 14A-B, configured to be received in matching pin receiving bores 258 (hidden from view), configured to guide first rigid member portion 250 and second rigid member portion 252 towards each other. It will be clear that other attachment mechanisms, known in the art for releasably attaching two components to each other, can be implemented by a skilled person in the art.

According to some embodiments, rigid member 242 further comprises rigid member protrusion 248. According to some embodiments, each of first rigid member portion 250 and second rigid member portion 252 include a portion of a rigid member protrusion (see FIGS. 14A-B), such that when first rigid member portion 250 and second rigid member portion 252 are attached to each other, both portions of the rigid member protrusion contact each other so as to form rigid member protrusion 248 (see FIG. 9B).

Advantageously, a rigid member 242 comprising two distinct portions that can be releasably attached to each other, provides simpler and easier operability by enabling quick placement of bag ventilator 10 on proximal base surface 204 when first rigid member portion 250 and second rigid member portion 252 are detached, then securing of bag ventilator 10 in position by attaching them to each other. Moreover, bag ventilator 10 can be removed in a quicker and simpler way from portable device for automated ventilation 100 by detaching first rigid member portion 250 and second rigid member portion 252. Advantageously, the disclosed configuration enables an operator of the device to quickly and easily switch between automated and manual bag ventilation.

According to some embodiments, a method of switching between automatic and manual bag ventilation includes accommodating bag ventilator 10 between proximal base surface 104, 204 and squeezing assembly 130, 230, initiating automatic operation of device 100, 200, so as to reciprocally squeeze and release the bag ventilator by drive mechanism 160, 260 via squeezing assembly 130, 230, interrupting the automatic operation of device 100, 200, and manually squeezing and releasing the bag ventilator by an operator's hands.

According to some embodiments, interrupting the automatic operation of device 100, 200 is manually performed by an operator, for example according to the state of the patient of reading from indicators on device 100, 200. According to some embodiments, interrupting the automatic operation of device 100, 200 is not voluntary, and occurs due to a malfunction of device 100, 200.

According to some embodiments, interrupting the automatic operation of device 100, 200 is facilitated by turning off the automatic operation of device 100, 200 via the at least one controller 126, 226. According to some embodiments, switching to manual ventilation further involves detachment of rigid member 142, 242 so as to provide easy and comfortable placement of an operator's hands on bag ventilator 10.

FIG. 11 constitutes a partial view in perspective of drive mechanism 260. Drive mechanism 260 comprises actuator 262 and transmission system 264 driven by actuator 262. Transmission system 264 comprises first pulley shaft 274 and second pulley shaft 276.

According to some embodiments, as exemplified in FIG. 11, transmission system 264 further comprises a first transmission pulley 294 rotateably attached to actuator 262 and configured to be driven thereby. Transmission system 264 further comprises a second transmission pulley 296, rotateably connected to first transmission pulley 294 via a first conveyor belt 298. First pulley shaft 274 is rigidly attached to second transmission pulley 296, configured to rotate in the same direction therewith. Second pulley shaft 276 is rotateably connected to first pulley shaft 274 via a second conveyor belt 278. First strap distal end 238 is rigidly attached to a distal surface of second conveyor belt 278, and second strap distal end 240 is rigidly attached to a proximal surface of second conveyor belt 278 (see FIG. 11).

In use, when bag ventilator 10 is accommodated within device 200 and squeezing assembly 230 is in a released state, actuator 262 is actuated so as to drive transmission system 264. Actuator 262 rotates first transmission pulley 294, which translates the rotational movement to second transmission pulley 296 via first conveyor belt 298. First pulley shaft 274, attached to second transmission pulley 296, rotates in the same direction therewith, while second transmission pulley 296 rotates in an opposite direction. The distal surface of second conveyor belt 278 moves in the direction of arrow 26 (see FIG. 11), pulling first strap portion 234 in the distal direction indicated by arrow 22, and the proximal surface of second conveyor belt 278 moves in the direction of arrow 28, pulling second strap portion 236 in the distal direction indicated by arrow 24.

When squeezing assembly 230 is in a pulled state, actuator 262 stops driving transmission system 264, such that all pulleys, including first pulley shaft 174 and second pulley shaft 176, are free to rotate in any direction. Squeezed bag ventilator 10 is self-inflating to its normally expanded form, pushing against rigid member 142, thereby extending first strap portion 234 and second strap portion 236 in the proximal direction, towards a released state of squeezing assembly 230.

Figure 12:
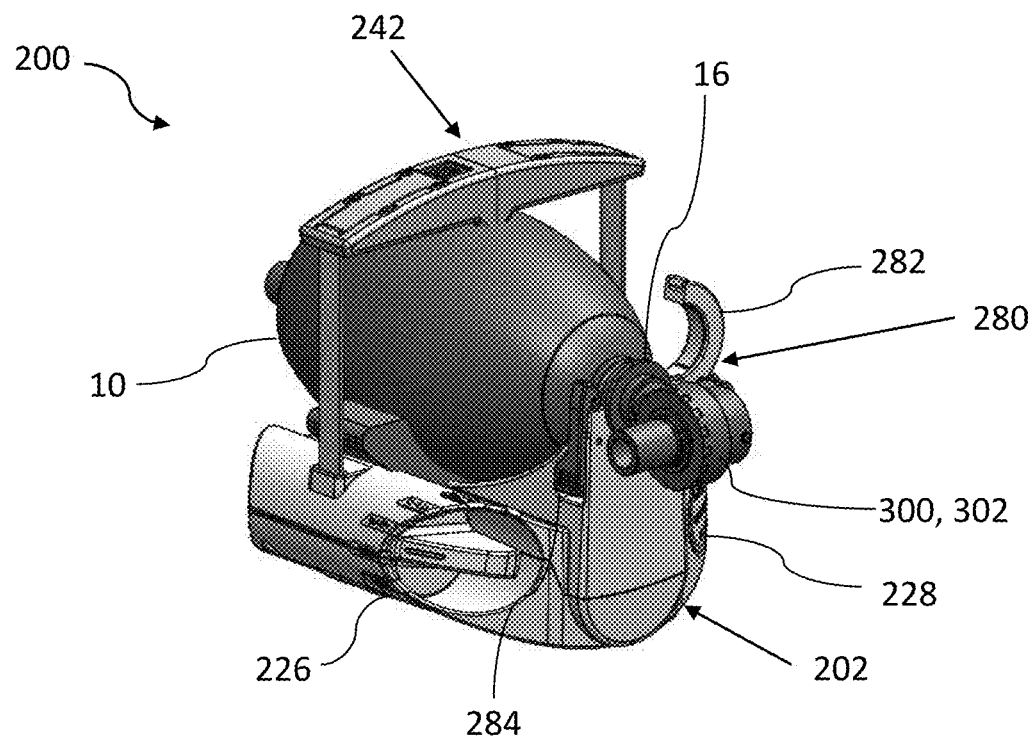
FIG. 12 constitutes a view in perspective of a portable device for automated ventilation, with a neck of a bag ventilator positioned on a beg-neck seat, according to some embodiments.
Figures 13A, 13B:
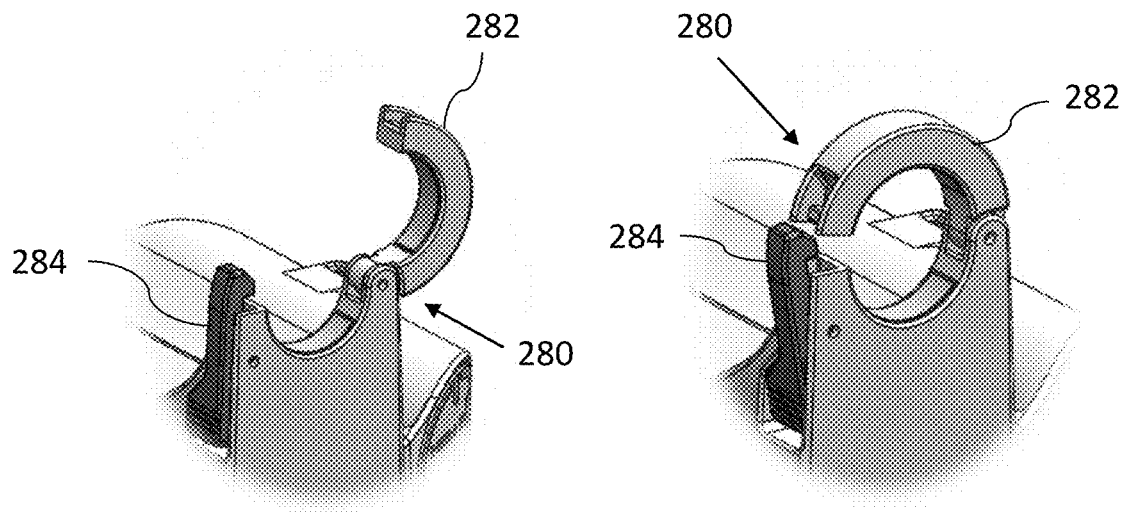
FIG. 13A constitutes a partial view in perspective of a beg-neck seat of a portable device for automated ventilation in a pre-locked state, according to some embodiments.
FIG. 13B constitutes a partial view in perspective of a beg-neck seat of a portable device for automated ventilation in an open state, according to some embodiments.

According to some embodiments, base body 202 further comprises a bag-neck seat 280, configured to accommodate a neck region 16 of bag ventilator 10 therein. FIGS. 12, 13A and 13B constitute a view in perspective of device 200 with neck region 16 of bag ventilator 10 positioned on beg-neck seat 280, and zoomed in views of beg-neck seat 280 in pre-locked and open states, respectively. Neck region 16 comprises a fastener 282 hinged thereto, and a latch 284 configured to interact with fastener 282.

An open state of beg-neck seat 280 (see FIGS. 12 and 13B) is a state in which fastener 282 is positioned away from latch 284, such that neck region 16 of bag ventilator 10 is free to move into and out of beg-neck seat 280 without interruption of fastener 282. A pre-locked state of beg-neck seat 280 (see FIG. 13A) is a state in which fastener 282 is positioned in proximity to latch 284, without interacting therewith yet, so as to abut neck region 16 when bag ventilator 10 is accommodated within device 200. A locked state of beg-neck seat 280 (not shown) is a state in which latch 284 interacts with fastener 282, so as to lock it in place.

Advantageously, beg-neck seat 280 enables fast and easy centralization of bag ventilator 10 when accommodated within device 200, as well as an additional stabilization mechanism for bag ventilator 10 when used in device 200, without requiring additional housing surrounding bag ventilator 10 for the same purpose.

According to some embodiments, base body 202 further comprises controller 226. In the example depicted in FIGS. 9B and 9D, controller 226 comprises a selection switch between three modes of operation, for example: children, small adult and large adult.

According to some embodiments, base body 202 further comprises indication zone 228. In the example depicted in FIGS. 9A-9D, indication zone 228 comprises three visual indicators, for indicating battery status (such as low battery), high-pressure and low-pressure.

FIGS. 15A and 15B constitute a view in perspective and a perspective bottom view of portable device for automated ventilation 200, according to some embodiments.

According to some embodiments, base body 202 further comprises power source compartment 288. According to some embodiments, base body 202 further comprises power supply socket 290. According to some embodiments, base body 202 further comprises data port 292. According to some embodiments, distal base surface 206 further comprises an attachment strap 286, configured for attaching device 200 either to external structures, such as structures within vehicles or storage facilities, stretchers and patient beds, or to a patient, such as to a patient's chest or a patient's arm. According to some embodiments, attachment strap 286 comprises an elastic material, such as rubber.

According to some embodiments, device 100, 200 further comprises at least one physiological sensing mechanism 300 (see FIGS. 1 and 12) configured to measure signals related to at least one physiological characteristic of a patient.

According to some embodiments, the at least one physiological sensing mechanism comprises at least one pressure sensor. According to some embodiments, the at least one physiological sensing mechanism comprises at least one $CO_2$ level sensor.

According to some embodiments, the at least one physiological sensing mechanism comprises a first sensing mechanism portion connected to a second sensing mechanism portion, such that the first sensing mechanism portion is attached to base body 102, 202 and electronically connected to the control circuitry of device 100, 200, and the second sensing mechanism portion is configured for positioning either between bag ventilator 10 and a breathing tube connectable thereto (not shown), or between bag ventilator 10 and a and a breathing mask connectable thereto (not shown). The second sensing mechanism portion of the at least one sensing mechanism comprises at least one sensor, such as a pressure sensor, a flow sensor, a $CO_2$ level sensor and the like, and is configured to electronically transmit the signals from the at least one sensor to the control circuitry of device 100, 200 via the first sensing mechanism portion.

According to some embodiments, the at least one physiological sensing mechanism comprises a plurality of sensors. According to some embodiments, the second sensing mechanism portion comprises a plurality of sensors, such as a pressure sensors and a $CO_2$ level sensor. According to some embodiments, device 100, 200 comprises a plurality of physiological sensing mechanisms.

According to some embodiments, the second sensing mechanism portion is detachably attached to the first sensing mechanism portion. According to some embodiments, the second sensing mechanism portion is disposable, and is configured to be replaced for each patient or for each use of device 100, 200.

According to some embodiments, device 100, 200 further comprises at least one operational sensing mechanism 302 (see FIGS. 1 and 12) configured to measure signals related to at least one operational characteristic of device 100, 200. The at least one operational sensing mechanism comprises at least one sensor, and is electronically connected to the control circuitry of device 100, 200. According to some embodiments, at least one operational sensing mechanism comprises at least one power-level sensor, such as battery-level sensor. According to some embodiments, the at least one operational sensing mechanism comprises at least one sensor configured to detect a mechanical failure of at least one component of device 100, 200. According to some embodiments, the at least one operational sensing mechanism comprises at least one sensor configured to detect electronic failure within the control circuitry of device 100, 200. According to some embodiments, device 100, 200 comprises a plurality of operational sensing mechanisms.

According to some embodiments, the readings of the at least one physiological sensing mechanism and the at least one operational sensing mechanism are indicated via at least one visual or auditory indicator of indication zone 128, 228. According to some embodiments, the readings of the at least one physiological sensing mechanism and the at least one operational sensing mechanism are transferred to the control circuitry, and the control circuitry is configured to adjust the operation of device 100, 200 accordingly.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although the invention is described in conjunction with specific embodiments thereof, it is evident that numerous alternatives, modifications and variations that are apparent to those skilled in the art may exist. It is to be understood that the invention is not necessarily limited in its application to the details of construction and the arrangement of the components and/or methods set forth herein. Other embodiments may be practiced, and an embodiment may be carried out in various ways. Accordingly, the invention embraces all such alternatives, modifications and variations that fall within the scope of the appended claims.

The invention claimed is:

1. A portable device for automated ventilation comprising:
   (i) a base body having a proximal base surface;
   (ii) a drive mechanism attached to the base body, the drive mechanism comprising an actuator and a transmission system configured to be driven thereby, the transmission system comprising a first pulley shaft and a second pulley shaft; and (iii) a squeezing assembly comprising a strap, the strap comprising a first strap portion having a first strap distal end, and a second strap portion having a second strap distal end, wherein the proximal base surface and the squeezing assembly are configured to accommodate a bag ventilator there between, wherein the first strap distal end and the second strap distal end are attached to the transmission system;

wherein the squeezing assembly is configured to be movable between a released state and a pulled state, and to reciprocate between these states for a plurality of cycles;

wherein the first pulley shaft and the second pulley shaft are configured to be rotatable in opposite directions, and wherein the first strap portion is movable by the first pulley shaft and the second strap portion is movable by the second pulley shaft.

2. The portable device for automated ventilation of claim 1, wherein the transmission system comprises a gear train, and wherein the first pulley shaft and the second pulley shaft are rotateably attached to the gear train.

3. The portable device for automated ventilation of claim 2, wherein the gear train comprises:
(i) a first gear connected to the actuator and rotatable thereby;
(ii) a second gear interconnected with the first gear;
(iii) a third gear interconnected with the first gear; and
(iv) a fourth gear interconnected with the third gear,
wherein the first pulley shaft is rigidly connected to the second gear, and
wherein the second pulley shaft is connected to the fourth gear.

4. The portable device for automated ventilation of claim 1, wherein the first strap distal end is rigidly attached to the first pulley shaft, and wherein the second strap distal end is rigidly attached to the second pulley shaft.

5. The portable device for automated ventilation of claim 1, wherein the transmission system comprises:
(i) a first transmission pulley, rotateably attached to the actuator and configured to be driven thereby;
(ii) a second transmission pulley;
(iii) a first conveyor belt; and
(iv) a second conveyor belt,
wherein the second transmission pulley is rotateably connected to the first transmission pulley via the first conveyor belt;
wherein the first pulley shaft is rigidly attached to the second transmission pulley, and is configured to rotate in the same direction therewith;
wherein the second pulley shaft is rotateably connected to the first pulley shaft via the second conveyor belt;
wherein the first strap distal end is rigidly attached to a distal surface of the second conveyor belt; and
wherein the second strap distal end is rigidly attached to a proximal surface of the second conveyor belt.

6. The portable device for automated ventilation of claim 1, wherein the proximal base surface comprises a base protrusion.

7. The portable device for automated ventilation of claim 1, wherein the squeezing assembly further comprises a rigid member connected to the strap.

8. The portable device for automated ventilation of claim 7, wherein the first strap portion and the second strap portion are two distinct separate straps, and wherein the rigid member is connected to the first strap portion and the second strap portion.

9. The portable device for automated ventilation of claim 8, wherein the rigid member comprises a first rigid member portion and a second rigid member portion detachably attached to each other, wherein the first strap portion is rigidly connected the first rigid member portion, and wherein the second strap portion is rigidly connected the second rigid member portion.

10. The portable device for automated ventilation of claim 7, wherein the rigid member comprises a rigid member protrusion.

11. The portable device for automated ventilation of claim 1, wherein the base body further comprises at least one of: a power supply socket, and/or a power source compartment configured to house at least one power source.

12. The portable device for automated ventilation of claim 1, wherein the base body further comprises a data port.

13. The portable device for automated ventilation of claim 1, wherein the base body further comprises a control circuitry for controlling the drive mechanism.

14. The portable device for automated ventilation of claim 1, wherein the base body further comprises at least one controller, configured for controlling functionality of the portable device for automated ventilation.

15. The portable device for automated ventilation of claim 1, wherein the base body further comprises an indication zone, configured to provide at least one visual or auditory indicator corresponding to a state of at least one characteristic of the portable device for automated ventilation.

16. The portable device for automated ventilation of claim 1, further comprising at least one physiological sensing mechanism configured to measure signals related to at least one physiological characteristic of a patient, wherein the physiological sensing mechanism comprises at least one of: a pressure sensor and/or a $CO_2$ level sensor.

17. The portable device for automated ventilation of claim 1, further comprising at least one operational sensing mechanism configured to measure signals related to at least one operational characteristic of portable device for automated ventilation.

18. The portable device for automated ventilation of claim 1, wherein the base body further comprises a distal base surface, and wherein the distal base surface comprises an attachment strap.

* * * * *